United States Patent
Markoll

[11] Patent Number: 6,048,302
[45] Date of Patent: Apr. 11, 2000

[54] APPARATUS FOR THE TREATMENT OF DISORDERS OF TISSUE AND/OR THE JOINTS

[75] Inventor: Richard Markoll, Boca Raton, Fla.

[73] Assignee: Bio-Magnetic Therapy Systems, Inc., Boca Raton, Fla.

[21] Appl. No.: 09/173,789

[22] Filed: Oct. 16, 1998

[30] Foreign Application Priority Data

Apr. 29, 1998 [DE] Germany .......................... 198 19 214

[51] Int. Cl.⁷ ............................................... A61B 17/52
[52] U.S. Cl. ............................................................. 600/13
[58] Field of Search .......................... 600/9–15; 128/897, 128/898

[56] References Cited

U.S. PATENT DOCUMENTS

| 435,343 | 8/1890 | Brown | 600/13 |
| 1,164,356 | 12/1915 | Kaiser | 600/13 |
| 3,658,051 | 4/1972 | MacLean | 600/13 |

*Primary Examiner*—Samuel Gilbert

[57] ABSTRACT

An apparatus for the treatment of disorders of tissue and/or the joints in the area of the jaw or neck of a patient (10), particularly for the treatment of periodontosis, is depicted, wherein the apparatus comprises a housing (4) that surrounds at least the area of the jaw or neck to be treated. A number of coils (6) is also provided for generating at least one electromagnetic field (E) which can be applied to the area to be treated. The coils (6) are arranged in the interior (5) of the housing (4).

5 Claims, 2 Drawing Sheets

APPARATUS FOR THE TREATMENT OF DISORDERS OF TISSUE AND/OR THE JOINTS

TECHNICAL FIELD

The invention relates to an apparatus for the treatment of tissue disorders and/or disorders of the joints (arthropathies) in the area of a patient's jaw or neck, particularly the treatment of periodontosis, using one or more electromagnetic fields.

PRIOR ART

The application of an electromagnetic field for the treatment of chronic disorders of the locomotor system, such as the joints, ligaments and back, is known in principle. Such disorders include for example arthroses, i.e. degenerative joint trouble, as well as tendinoses, degenerative ligamentary and tendinous trouble, rheumatic disorders such as inflammatory disorders of the joints, and acute injuries caused by sports-related or industrial accidents.

In this way, the Applicant's patents U.S. Pat. No. 5,131,904 or U.S. Pat. No. 5,453,073 for example show an apparatus for the application of an electromagnetic field in order to treat inflammatory or degenerative disorders of the joints, especially arthrosis.

An organ of the body to be treated, such as a limb, a section of the spinal column, an elbow or knee joint, is placed inside an annular coil. Because the organ of the body to be treated is arranged in this way within the aperture of the annular coil, it is possible to transfer an electromagnetic field induced by the annular coil to the organ of the body to be treated. The healing process within the affected organ of the body can be promoted by the applied electromagnetic field. The electromagnetic field causes endogenous regeneration to be stimulated and cartilage or connective tissue in the diseased organ of the body to be continuously regenerated.

It has, however, also been shown that diseased tissue or joints of the area of a patient's jaw and neck cannot be effectively treated using the known apparatus. In this way, specific treatment of atrophy of the periodontal tissue, i.e. gums, alveolar periosteum and alveolar bone, or arthrosis of the temporomandibular joint cannot be effectively performed because it is extremely difficult for the jaw area to be treated to be positioned correctly within the annular coil such that the electromagnetic field is selectively applied only on the periodontal tissue and/or temporomandibular joint and can take effect directly at the site of treatment. The known apparatus therefore cannot be used for the effective treatment of specific disorders of the area of the jaw, such as periodontosis or arthrosis of the temporomandibular joint, not to mention the area of the throat and neck, such as whiplash injuries, muscle strains and degenerative trouble.

DESCRIPTION OF THE INVENTION

In view of these drawbacks and remaining problems associated with the apparatus known in the prior art, the present invention is based upon the object of providing an apparatus which ensures with minimum structural design outlay a systematic and effective application of at least one electromagnetic field to tissue to be treated and/or to a joint or joints to be treated in the area of a patient's jaw or neck.

This object is solved by an apparatus according to the invention comprising the features of claim 1.

According to the invention, the apparatus for the treatment of tissue disorders and/or arthropathies in the area of a patient's jaw or neck, particularly for the treatment of periodontosis, comprises a housing which surrounds in an ergonomically beneficial manner at least the area of the jaw or neck to be treated. It is therefore possible to place the housing on the patient's head very close to or directly over the tissue and/or temporomandibular joint to be treated. The housing according to the invention is made from any suitable material, though particularly from plastic, e.g. polyethylene, polypropylene or the like, or a suitable metal, e.g. aluminum. The use of plastic ensures a particularly lightweight structure for the housing. Savings can also be achieved in terms of the housing's weight and material by designing the housing to have a shell-shaped structure. Advantages in terms of production technique are also obtained by designing the housing according to the invention as a molded plastic part.

A number of coils is also arranged within the housing; these coils generate at least one electromagnetic field. The electromagnetic field or fields induced in the coils is or are applied to the area to be treated, whereby the healing process in the tissue or joint to be treated can be stimulated by the electromagnetic field energy. As far as the patient is concerned, the electromagnetic field is applied at the center of treatment completely without pain, without having to operate at the treatment site. The individual coils are also accommodated within the housing such that they are reliably supported and secured inside the housing. As a result of this layout, the coils are positioned in the housing in a manner that protects them from outside effects or influences, such as impacts, dirt accumulation or tampering. The size of the housing depends on the expansion and number of the coils disposed therein and is dimensioned to be at least so large that all the coils can be completely received therein.

The treatment apparatus described not only makes it possible to provide in a simple and effective manner a housing shape that is adapted to the shape of the jaw and neck and which is consequently very beneficial in ergonomic terms, but also allows the electromagnetic fields generated by the individual magnetic coils to be systematically applied to different areas of the jaw or neck, particularly to the periodontal tissue in the jaw, since the coils located inside the housing can be guided very close to the center of treatment and directly placed there. The provision of a number of coils always ensures that at least one coil ends up over the respective center of treatment in the jaw or neck area. According to the invention, the distance between the respective treatment center and the particular coil closest thereto is reduced to a minimum. As a result, the flux lines of the electromagnetic field or fields must travel only a very short path to the treatment site. The strength and intensity of the electromagnetic fields generated in the coils is therefore almost completely maintained at the site of treatment, i.e. in the periodontal tissue, on the temporomandibular joint and/or nuchal tissue, ensuring a particularly effective application of the electromagnetic field to the diseased tissue or joint. Compared with conventional apparatus in which large surface areas of an organ of the body are subjected to the electromagnetic field, the magnetic field's flux lines can therefore be selectively aligned with the periodontal tissue, temporomandibular joint or nuchal musculature and systematically applied there.

Advantageous embodiments of the invention are described in the further claims.

According to an advantageous design feature of the invention, the housing has a U-shaped contour. Designing the housing to be U-shaped advantageously adapts the housing to the outer contour of the patient's head in the area of the jaw and neck. In the case of periodontosis treatment, the patient's head is arranged between the two shanks of the U-shaped housing so that the housing extends substantially along the outer contour of the jaw from one temporomandibular joint to the other and across the front of the head. When treating trouble in the neck area, e.g. whiplash injuries, muscle strains or degenerative trouble, on the other hand, the housing is arranged at the rear of the head, with the two shanks of the U-shaped housing substantially encompassing the neck area and partial areas of the patient's head. The distance between both the shanks of the housing is chosen such that the head of a patient can be comfortably placed between the two shanks.

Preference is given to providing a positioning means for positioning the housing at least over the jaw or neck area to be treated. The housing's attachment to the positioning means can in principle be of a detachable design. The housing is preferably rotatably and pivotably connected to the positioning means via an arbitrary connecting means, such as a screw or clamping connection or a connecting joint, and is kept in place thereby at the height of the area of the patient's neck and head. The positioning means can be advantageously moved in the direction of the X, Y and Z axes and is rotatable around the respective axes and hence can be arbitrarily positioned so that the housing secured to the positioning means can be positioned to optimum effect over the tissue and/or joint to be treated in the area of a patient's jaw or neck. The use of a known, commercially available positioning means which is arbitrarily variable and adjustable in terms of position offers the advantage of a particularly inexpensive structural design. Attaching the housing to the positioning means considerably simplifies the overall apparatus structure's handling. This advantage is particularly effective when the electromagnetic field generated by the coils inside the housing is aligned with the center of treatment.

To create an effective electromagnetic field, it has proved advantageous for the coils within the housing to be distributed at a predetermined distance from one other and/or preferably along the entire U-shaped contour of the housing. The distance between adjacent coils is preferably set such that the electromagnetic fields generated by the coils each overlap in the area between two adjacent coils, causing the field density and strength to be increased at the sites of overlap. This allows the intensity of treatment to be enhanced and the healing process within the tissue to be additionally stimulated. It has been shown that the tissue absorbs and conducts the electromagnetic energy emitted by the coils, i.e. during the treatment process, the energy applied to the tissue is evenly distributed across the entire tissue to be treated. It is therefore also possible to supply electromagnetic energy to those areas of the jaw tissue or neck which are not in direct proximity to a coil and to activate the healing process there. In consequence, it has proved to be particularly beneficial when treating periodontosis for the coils to be distributed at a constant distance along the U-shaped contour of the housing, enabling the electromagnetic fields generated by the individual coils to be evenly applied to the entire periodontal tissue.

It has proved to be particularly beneficial for at least seven coils to be spaced apart from one another within the housing. This configuration made it possible in practice to achieve particularly positive treatment results.

To make it simple to fit the coils within the housing, the housing is preferably composed of at least two thin-walled housing members. The two housing members are each essentially U-shaped along their longitudinal extension, whereby when fitted together, both housing members surround a hollow space. To support the coils reliably within the hollow space formed between the shell-like housing members, there are advantages if the housing members each have a rectangular cross-sectional contour. The housing members can also, however, exhibit any other cross-sectional shapes, for example a semicircular or polygonal configuration is conceivable. To avoid access from outside or to prevent dirt from penetrating into the interior of the housing, it is advantageous for the two housing members to adjoin one another substantially along their edges and/or to overlap at their edge portions. As a result, it is possible to reduce the risk that contaminants penetrate into the interior of the housing and into the coils, that the surfaces of the coils clog up and as a consequence adversely affect the quality of the electromagnetic field's transmission power upon the area to be treated.

To prevent the coils from overheating inside the housing, it has been shown to be positive to provide ventilation apertures between at least two housing members. The ventilation apertures are advantageously formed between the substantially adjacent and/or overlapping edge portions of the housing members. This can for example be achieved in that when assembling the housing, a distance is maintained between the edge portions of the housing members as a result of providing suitable spacers. The ventilation apertures can also, however, simply be drilled through the housing casing or cut through it so as to ensure adequate ventilation inside the housing and temperature equalization within the housing for reliable operation.

According to a further embodiment of the invention, the housing comprises at least two arms which are connected together in a revolving manner. The two arms advantageously form the two shanks of the U-shaped housing. This embodiment makes it possible to guide the coils arranged in the arms of the housing as close as possible to the patient's head and hence to the particular center of treatment. By pivoting the arms around their point of rotation toward the patient's head, the coils are placed directly over the site of treatment, enabling the electromagnetic field generated by the coils to be applied directly and with a high intensity. This embodiment also enjoys the major advantage that the housing can be adapted to the size and shape of the particular patient's head and that the housing can also be accurately positioned when patients have different shapes of head. Four coils are preferably arranged in one arm and three coils in the other, or vice versa.

Another advantageous embodiment feature of the invention envisages that the coils each have a core which is respectively surrounded by a number of wire windings. The insertion of a core into the annular coil composed of the wire windings entails the advantage that the magnetic field is additionally enhanced. The use of a ferrite core is preferred because as a result the electromagnetic fields generated in the coils develop the desired intensities and propagation characteristics. The wire for the windings comprises an arbitrary conductive material, such as copper, with the number of windings and the wire's diameter influencing the strength of the field to be generated.

It has also proved to be beneficial for the center axes of the coils arranged in the housing to be respectively directed at the area to be treated. In doing so, the center axes are oriented substantially at right angles to the surface of the area to be treated on the patient's head. The center axes extend substantially parallel to the orientation of the flux lines inside the coils. The flux lines are therefore aligned or oriented toward the center of treatment. As a result, a particularly effective transfer of the electromagnetic fields generated by the coils to the tissue and/or joint to be treated can be advantageously ensured since the flux lines move directly toward the area of tissue or joint to be treated and penetrate same.

According to another preferred embodiment of the invention, means for operating the coil with a pulsed d.c. voltage is provided. The coils arranged in the housing are excited by the pulsed d.c. voltage which preferably exhibits an abruptly ascending and abruptly descending rectangular waveform. The voltage preferably pulses at a frequency of 1 to 30 pulses per second to generate an electromagnetic field in the coil of less than 20 Gauss. Advantages are gained if the electromagnetic fields generated by the individual coils are each identical, i.e. exhibit the same d.c. voltage and field strength. This arrangement has proved to be particularly advantageous when treating periodontosis and disorders of the temporomandibular joint. It is beneficial if a display which is easily visible to the user is attached for example to the outside of the housing; such a display indicates coil operation, i.e. an excited electromagnetic field, and makes it possible to identify the respective treatment site. As a result, the duration and nature of treatment (treatment of periodontosis, the temporomandibular joint and/or neck) is identifiable and can be monitored by the user. Such a display may for example be of the LED type.

In this context, it is also advantageous for the coil operating means to comprise control means with which a predetermined sequence of treatment periods and the length of treatment periods can be automatically controlled. It has been shown that particularly good treatment results can be achieved by a sequence of 2×5 and 1×50 minutes. The control means preferably comprises a circuit arranged on the control means or on the housing.

As regards systematic application of the electromagnetic fields to the particular tissue or joint to be treated in the area of the jaw or neck, it is beneficial that the coils can be optionally operated jointly or independently of one another. In this way, the coils are connected in parallel for example for treatment of periodontosis in which the electromagnetic fields are to be applied along the entire area of the jaw. This ensures that the electromagnetic fields generated by the individual coils are evenly applied to the periodontal tissue. When treating arthrosis of the temporomandibular joint, on the other hand, it has been shown to be positive to operate just that coil which is arranged over the particular temporomandibular joint to be treated, i.e. one of the two outer coils in the U-shaped housing. The electromagnetic fields can therefore be switched between the individual coils by the control means so that depending on the nature of treatment, the coil or coils located over the center of treatment can also be selectively operated. This selective application of the electromagnetic fields just to the respective center of treatment made it possible to achieve particularly effective and positive treatment results in the past.

BRIEF DESCRIPTION OF THE DRAWINGS

The invention will now be explained in further detail on the basis of the embodiments depicted by way of example in the drawings.

To avoid repetitions, identical parts and components will also be identified by the same reference symbols in the following description and drawings, unless it is necessary to draw further distinctions.

DETAILED DESCRIPTION OF THE INVENTION'S EMBODIMENTS

Figure 1:
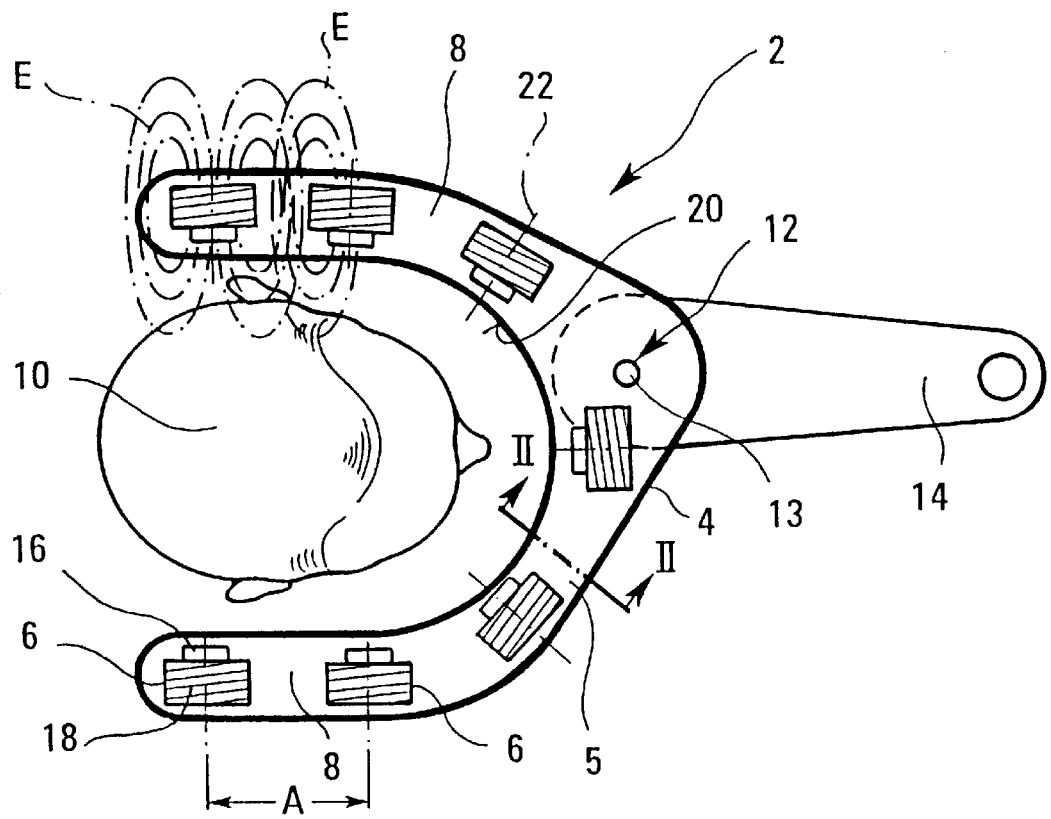
FIG. 1 shows a partially cut-away top view of a first embodiment of a treatment apparatus according to the invention.

As can be identified in FIG. 1, which shows a partially cut-away top view of a first embodiment of the apparatus 2 according to the invention for the treatment of tissue disorders and/or arthropathies in the area of the jaw or neck of a patient 10, a U-shaped housing 4 comprises a total of seven coils 6 in its interior 5. The housing 4 is shell-shaped and has two arms 8 which are arranged around the jaw area of a patient 10. The U-shaped housing 4 surrounds the entire jaw of the patient 10, including the area above the left and right temporomandibular joints. The two arms 8 of the housing 4 are connected together in a revolving manner in the bight of the U-shaped housing (FIG. 1) by means of a hinge joint 12 and are made from a non-transparent plastic material, e.g. polyethylene or polypropylene, as a molded plastic part. The arms 8 form, in their interior 5, a hollow space for receiving the coils 6. Four coils 6 in total are supported in the arm 8 shown in the top view on the left next to the head, while three coils 6 in total are supported in the arm 8 disposed on the right next to the head. The spaces formed between the inner housing wall and the coil surfaces are foam-filled by a suitable plastic material.

A positioning means, which cannot be identified in FIG. 1, is rotatably arranged on the housing 4 by means of a connecting element 14. In the present case, the connecting element 14 is attached in the hinge joint 12 via a pin 13 and is pivotable on the drawing plane.

The coils 6 shown in FIG. 1 each comprise ferrite cores 16, with copper wire windings 18 being wound around the periphery of a particular core 16. The coils 6 in the housing 4 are distributed at a predetermined distance from one another along the entire U-shaped contour of the housing 4. The distance A between adjacent coils 6 is calculated such that the electromagnetic fields E generated by the coils 6 overlap in the area between two adjacent coils, as indicated in FIG. 1 by broken lines.

The individual coils 6 are connected together in an electrically conductive manner, for example via cables (not shown), and connected to coil operating means (not shown). When the coil operating means is switched on, an electromagnetic field E with an equal field strength is induced in each of the coils 6. The coil operating means is connected to a control means (not shown in FIG. 1) whose circuit is integrated in the connecting element 14. Operating the control means also makes it possible to supply just individual coils 6 with current, allowing the coils 6 to be optionally operated jointly or independently of one another. The electromagnetic field E induced by the applied voltage in the coils 6 is applied to the jaw area of the patient 10. For this purpose, the housing 4 is made from a material, in this particular instance plastic, which does not affect the electromagnetic fields E generated by the coils 6, so that the fields penetrate outwards from the housing 4 without interruption and are applied to the tissue or temporomandibular joint of the patient 10.

The head of the patient 10 located between the two arms 8 of the housing 4 is guided as close as possible to an inner side 20 of the housing 4. The two arms 8 are also pivoted via the hinge joint 12 toward the head of the patient 10 until they make contact with his head. This ensures that the coils 6 are placed adjacent (FIG. 1) the head of the patient 10 directly beside the area to be treated. The coils 6 are positioned in the housing 4 in such a way that the coils' center axes 22, which extend parallel to the course of the flux lines within the coils 6, are directed at the particular center of treatment.

Figure 2:
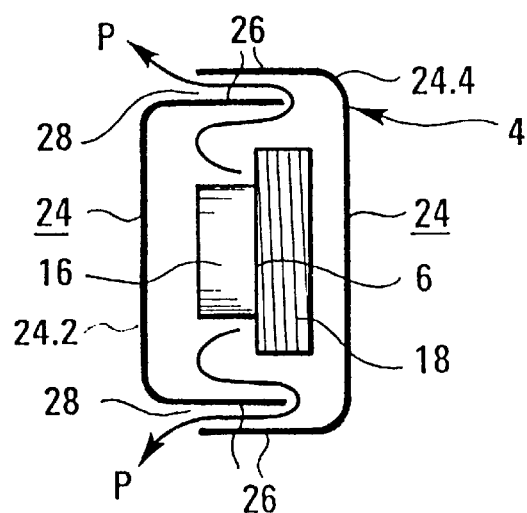
FIG. 2 shows an enlarged, schematic sectional view of the housing of the treatment apparatus according to the invention as part of the first embodiment.

FIG. 2 shows an enlarged schematic sectional view of the housing 4 of the treatment apparatus along the line II—II according to FIG. 1. As can be identified in FIG. 2, the housing 4 is composed of two thin-walled housing members 24. The two housing members 24 each have a shell-shaped or U-shaped cross-sectional form. In the present case, one housing member 24.2 points toward the face or head of the patient 10, while a housing member 24.4 forms that side of the housing 4 which faces away from the head of the patient 10. The housing member 24.2 has a slightly smaller height than the housing member 24.4, so that the housing member 24.2 can be easily inserted into the housing member 24.4. During assembly, the coils 6 are inserted into the outer housing casing 24.4 and then the inner housing casing 24.2 is inserted into the housing casing 24.4 in order to seal the housing 4 above the coils 6. To secure the two housing members 24 together, they are suitably screwed together and/or sealed up. As can be clearly identified in FIG. 2, the two housing members 24 overlap at their respective edge portions 26. The edge portions 26 of the inner housing casing 24.2 (facing toward the head) and outer housing casing 24.4 (facing away from the head) end up spaced apart from one another in the area of overlap. The spaces formed in this way between the edge portions 26 serve as ventilation apertures 28 for ventilating the housing interior 5. As indicated in FIG. 2 by two arrows P, the ventilation apertures 28 therefore enable the heat generated during operation of the coils 6 to penetrate outwards from the housing interior 5. This ensures that the heat generated by the coils 6 is dissipated to an optimum extent.

Figure 3:
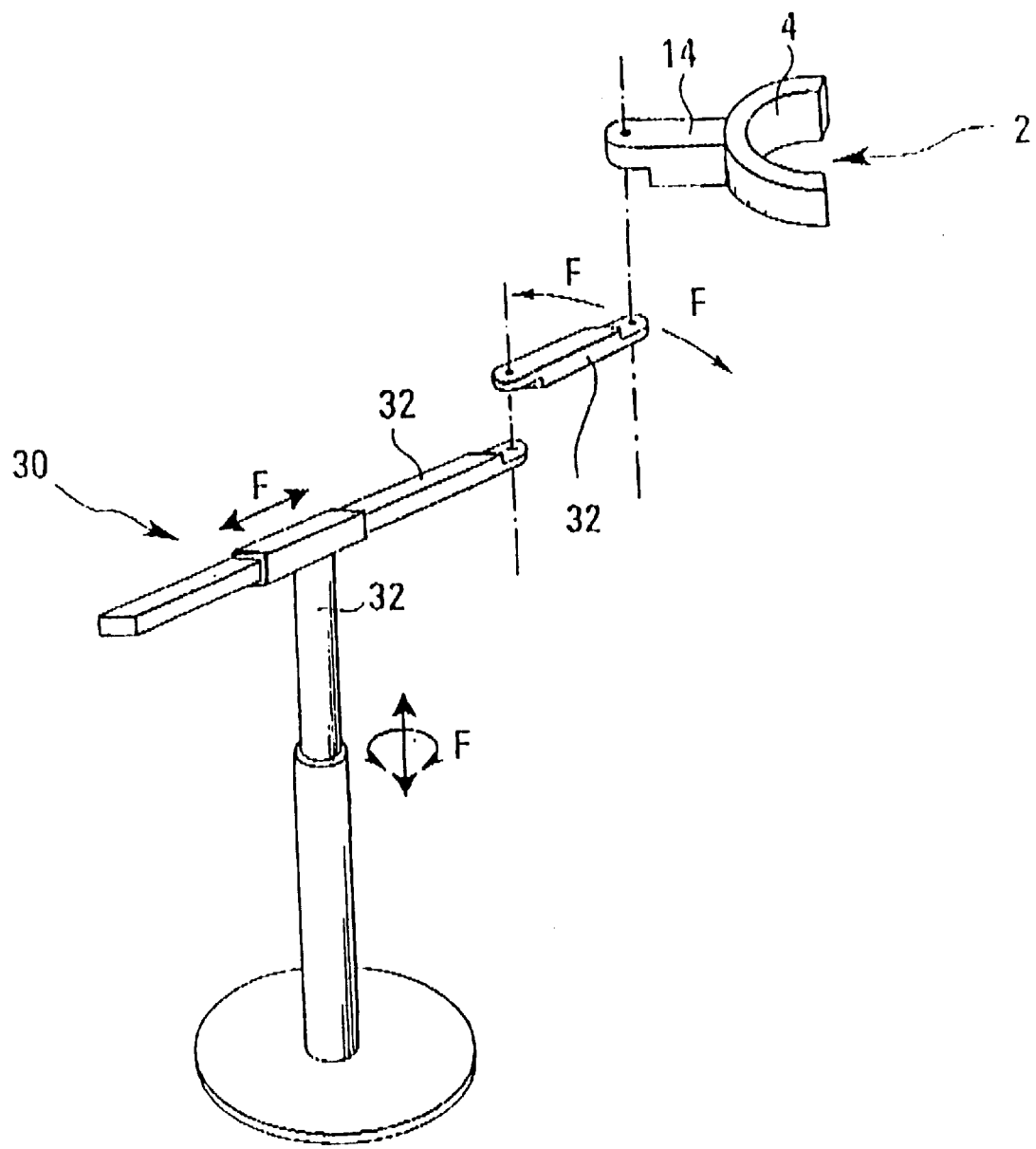
FIG. 3 shows an exploded perspective view of a second embodiment of the treatment apparatus according to the invention.

The second embodiment of the treatment apparatus according to the invention, as shown in the exploded perspective view in FIG. 3, essentially differs from the one in FIG. 1 in that a positioning means 30 for the housing 4 can also be identified. The structure and functioning of the housing 4 and the coils 6 located therein are essentially similar to the embodiment shown in FIG. 1. Unlike the apparatus 2 shown in FIG. 1, the housing 4 is, however, rigidly connected to the connecting element 14. The movement of the housing 4 for positioning on an area to be treated on the patient's head is solely brought about by the positioning means 30.

As can be identified in FIG. 3, the positioning means 30 comprises a plurality of levers 32 which are hingedly connected together or which can be shifted against or into one another. The housing 4 can be arbitrarily positioned via the positioning means 30, as indicated by arrow F in FIG. 3, and can in particular be accurately placed over the area of treatment on the head of the patient 10.

The invention is not restricted to the embodiments explained above, which merely represent general notional examples. On the contrary, the treatment apparatus according to the invention may differ considerably from the above exemplary embodiments. For example, the housing according to the invention may be made from a suitable material other than plastic or metal. More or fewer than seven coils can also be accommodated in the housing, depending on the desired intensity of treatment. The positioning means can also be of any other design that would allow an exact, simple and easy-to-handle positioning of the housing in the area of the patient's jaw or neck. For this purpose, the levers of the positioning means shown in FIG. 3 can also, for example, be fitted with upwardly or downwardly mobile hinge joints.

I claim:

1. Apparatus for treating the jaw area of a patient comprising:
   a. a hollow U-shaped plastic housing comprising a pair of arms pivotally secured together in the bight of the "U", the housing adapted to be horizontally disposed and receive the jaw area,
   b. a plurality of electro-magnets mounted inside the housing, each magnet comprising a ferrite core having an axis directed horizontally at the jaw area, and copper windings on the respective cores,
   c. a power supply connected to the windings and structured to generate a pulsed D.C. current for producing in the coils a field of less than 20 Gaus, pulsing at a rate of 1 to 30 pulses per second.

2. An apparatus as claimed in claim 1 wherein the housing is formed with slots to permit ventilation.

3. An apparatus as claimed in claim 1 wherein control means connect the coils individually or together in parallel to the power supply.

4. An apparatus as claimed in claim 1 including means tor supporting the U-shaped housing to provide lateral or vertical adjustability.

5. A method of treating the jaw area comprising:
   a. providing a horizontally disposed hollow U-shaped plastic housing defined by a pair of arms pivotally secured together in the bight of the U-shaped housing, a plurality of electro-magnets mounted inside the housing, each comprising a ferrite core having windings directed inward of the U-shaped housing and electrically conductive windings on the core,
   b. providing a power supply connected to the windings and structured to generate a pulsed D.C. current for producing in selected coils a field of less than 20 Gaus pulsing at a rate of 1 to 30 pulses per second,
   c. placing a patient adjacent the housing with the arms in open position and pivoting the arms of the U-shaped housing closed to positions closely adjacent the respective sides of the jaw of the patient.

* * * * *